(12) United States Patent
Okino et al.

(10) Patent No.: US 10,845,348 B2
(45) Date of Patent: Nov. 24, 2020

(54) GAS SENSOR AND GAS SENSING SYSTEM

(71) Applicant: Panasonic Intellectual Property Management Co., Ltd., Osaka (JP)

(72) Inventors: Toru Okino, Osaka (JP); Yutaka Hirose, Kyoto (JP); Yoshihisa Kato, Hyogo (JP); Akio Oki, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 275 days.

(21) Appl. No.: 16/005,995

(22) Filed: Jun. 12, 2018

(65) Prior Publication Data

US 2018/0292347 A1 Oct. 11, 2018

Related U.S. Application Data

(63) Continuation of application No. PCT/JP2016/005115, filed on Dec. 13, 2016.

(30) Foreign Application Priority Data

Dec. 16, 2015 (JP) ................. 2015-245716

(51) Int. Cl.
*G01N 33/00* (2006.01)
*G01N 27/414* (2006.01)
*G01N 27/403* (2006.01)

(52) U.S. Cl.
CPC ....... *G01N 33/0031* (2013.01); *G01N 27/403* (2013.01); *G01N 27/4148* (2013.01); *G01N 27/4141* (2013.01)

(58) Field of Classification Search
CPC .......... G01N 27/4141; G01N 27/4148; G01N 33/0031
See application file for complete search history.

(56) References Cited

U.S. PATENT DOCUMENTS

| 6,187,597 | B1* | 2/2001 | Lundstrom | ........ | G01N 33/0031 422/98 |
| 2010/0188110 | A1* | 7/2010 | Sun | ................. | G01N 33/0031 324/694 |
| 2012/0000274 | A1 | 1/2012 | Fife | | |
| 2012/0001237 | A1 | 1/2012 | Fife et al. | | |

(Continued)

FOREIGN PATENT DOCUMENTS

| JP | S59-142452 A | 8/1984 |
| JP | 2004-085392 A | 3/2004 |

(Continued)

OTHER PUBLICATIONS

International Search Report issued in Application No. PCT/JP2016/005115 dated Mar. 21, 2017, with English translation.

*Primary Examiner* — Paul M. West
(74) *Attorney, Agent, or Firm* — McDermott Will & Emery LLP

(57) ABSTRACT

A gas sensor includes: a cell array which includes a plurality of cells disposed in rows and columns; a read-out circuit which reads out signals from the plurality of cells; and a signal processor which processes the signals read out. Each of the plurality of cells includes: a gas molecule detector which is electrically isolated between adjacent ones of the plurality of cells; and an amplifier circuit which is electrically connected to the gas molecule detector.

17 Claims, 20 Drawing Sheets

(56) References Cited

U.S. PATENT DOCUMENTS

2012/0001615 A1    1/2012   Levine
2013/0200373 A1    8/2013   Murai et al.
2013/0281325 A1   10/2013   Elibol et al.
2016/0003770 A1    1/2016   Klootwijk et al.

FOREIGN PATENT DOCUMENTS

| | | |
|---|---|---|
| JP | 2006-133083 A | 5/2006 |
| JP | 2012-112651 A | 6/2012 |
| JP | 2013-533482 A | 8/2013 |
| JP | 2015-504522 A | 2/2015 |
| JP | 2015-531491 A | 11/2015 |
| JP | 2015-225950 A | 12/2015 |
| WO | 5410605 B2 | 2/2014 |

\* cited by examiner

FIG. 10B

| TIME | | CELL | | | | | | | | |
|---|---|---|---|---|---|---|---|---|---|---|
| | | a | b | c | d | e | f | g | h | i |
| | t0 | + | + | − | − | − | − | − | − | − |
| | t1 | + | + | + | − | − | − | − | − | − |
| | t2 | + | − | + | + | − | − | − | − | − |
| | t3 | + | + | − | + | + | − | − | − | − |
| | t4 | + | + | + | − | + | + | − | − | − |
| | t5 | + | − | + | + | − | + | + | − | − |
| | t6 | + | + | − | + | + | − | + | + | − |
| | t7 | − | + | + | − | + | + | − | + | + |
| | t8 | − | − | + | + | − | + | + | − | + |
| | t9 | − | − | − | + | + | − | + | + | − |
| | t10 | − | − | − | − | + | + | − | + | + |
| | t11 | − | − | − | − | − | − | + | − | + |
| | t12 | − | − | − | − | − | − | + | + | − |
| | t13 | − | − | − | − | − | − | − | + | + |
| | t14 | − | − | − | − | − | − | − | − | + |

GAS SENSOR AND GAS SENSING SYSTEM

CROSS REFERENCE TO RELATED APPLICATIONS

This application is a U.S. continuation application of PCT International Patent Application Number PCT/JP2016/005115 filed on Dec. 13, 2016, claiming the benefit of priority of Japanese Patent Application Number 2015-245716 filed on Dec. 16, 2015, the entire contents of which are hereby incorporated by reference.

BACKGROUND

1. Technical Field

The present disclosure relates to a gas sensor and a gas sensing system including the gas sensor.

2. Description of the Related Art

Gas sensors have been introduced not only to industrial fields such as semiconductor production factories and chemical plants, but also to homes. Gas sensors are widely used as devices which prevent gas-related accidents. The type of gas which is detected by the devices which prevent gas-related accidents is limited, depending on their usage, to gas such as $H_2$, chlorofluorocarbon, carbon monoxide (CO), and nitric oxide (NO). Moreover, the concentration necessary for detection is also as high as a ppm (parts per million) order to a percentage order. Various types of gas sensors have already been commercialized (for example, a semiconductor type gas sensor using tin oxide ($SnO_2$), a contact combustion type gas sensor using a catalyst, and an electrochemistry type gas sensor, etc.).

In recent years, gas sensors have been further developed not only to be used for preventing gas-related accidents, but also for the environmental monitoring aiming environmental preservation and for detecting disease-related volatile organic compounds (VOC) included in expiration. In the above-mentioned uses, many types of gas should be detected, the concentration necessary for detection is as low as from a ppt (parts per trillion) order to a ppb (parts per billion) order, and highly sensitive detection is necessary.

Japanese Unexamined Patent Application Publication No. 2012-112651 discloses a sensor element which detects the presence and the content of a target chemical substance by calculating change in the resistance value of a metallic oxide.

Furthermore, Japanese Unexamined Patent Application Publication No. 59-142452 discloses an ion sensor in which a metal gate is provided on a gate insulating film of an insulating film gate field-effect transistor, and an ion sensitive membrane is formed on an extended part of the metal gate.

Moreover, Japanese Unexamined Patent Application Publication No. 2004-085392 discloses a chemical sensor including a field-effect transistor in which a carbon element linear structure is formed on the gate electrode.

SUMMARY

In the sensor element disclosed in Japanese Unexamined Patent Application Publication No. 2012-112651, a temperature controller is provided to obtain sufficient detection sensitivity to a target chemical substance. This is because it is necessary to control the sensor element such that the sensor element is at a temperature suitable for a reaction of the target chemical substance to create an environment in which the resistance value changes greatly, i.e., an environment with many reactions. Moreover, with the sensor element disclosed in Japanese Unexamined Patent Application Publication No. 2012-112651, in order to perform a reset operation, it is necessary to maintain the equilibrium situation of a reversible reaction, and the reset operation is also considered to be performed by the temperature controller.

Therefore, the gas sensor disclosed in Japanese Unexamined Patent Application Publication No. 2012-112651 which requires a temperature controller becomes large in size, and it is difficult to produce a small portable product. Furthermore, performing the temperature control requires more cost of the electric power.

Moreover, in the sensor element disclosed in Japanese Unexamined Patent Application Publication No. 59-142452, the electric double layer (potential difference) corresponding to an ion concentration is formed on the surface of the ion sensitive membrane, and the change in the electric current between the source and the drain according to the change in the potential difference is read out. Since a signal component is large compared to the thermal noise component of electric current, it is necessary to increase the potential difference. Consequently, the ion sensitive membrane, i.e., the area of the sensor needs to be enlarged. Therefore, even when the sensor structure disclosed in Japanese Unexamined Patent Application Publication No. 59-142452 is used, the sensor structure becomes large in size as with the sensor structure disclosed in Japanese Unexamined. Patent Application Publication No. 2012-112651. Thus, it is difficult to produce a small portable product.

Moreover, in order to enhance detection sensitivity effectually without increasing the planar surface area of a gate electrode, the sensor element disclosed in Japanese Unexamined Patent Application Publication No. 2004-085392 includes, on the gate electrode, a carbon element linear structure represented by a carbon nanotube, which is a nanomaterial having a very large aspect ratio. Even when the structure of the sensor disclosed in Japanese Unexamined Patent Application Publication No. 2004-085392 is used, the planar surface area of the gate electrode does not become large. However, a certain amount of area is required to obtain sufficient sensitivity, and it is difficult to further miniaturize the sensor.

The present disclosure is conceived in view of the actual circumstances of the above conventional techniques, and has an object to provide a low cost and small gas sensor.

In order to solve the above problems of the conventional techniques, a gas sensor according to one aspect of the present disclosure includes: a cell array which includes a plurality of cells disposed in rows and columns; a read-out circuit which reads out signals from the plurality of cells; and a signal processor which processes the signals read out. Each of the plurality of cells includes: a gas molecule detector which is electrically isolated between adjacent ones of the plurality of cells; and an amplifier circuit which is electrically connected to the gas molecule detector.

According to the present disclosure, a low cost and small gas sensor can be provided.

BRIEF DESCRIPTION OF DRAWINGS

These and other objects, advantages and features of the disclosure will become apparent from the following descrip

FIG. 10B is a timing chart showing polarities of power supply potentials of reset transistors of the cells.

DETAILED DESCRIPTION OF THE EMBODIMENTS

The following describes embodiments of a gas sensor and a gas sensing system including the gas sensor according to the present disclosure with reference to the drawings. Note that, although the present disclosure is described with reference to the following embodiments and the attached drawings, these are mere examples and do not intended to limit the present disclosure. Therefore, numerical values, shapes, materials, structural components, arrangement positions and connection configuration of the structural components, steps, and an order of the steps shown in the following embodiments are mere examples, and are not intended to limit the present disclosure. The present disclosure is limited only by what is claimed. Therefore, among the structural components in the embodiments below, structural components not recited in any one of independent claims which indicate the broadest concepts of the present disclosure are described as not necessarily required to achieve problems of the present disclosure, but described as configuring more preferred embodiments.

Embodiment 1

A gas sensor according to Embodiment 1 is described.

Figure 1:
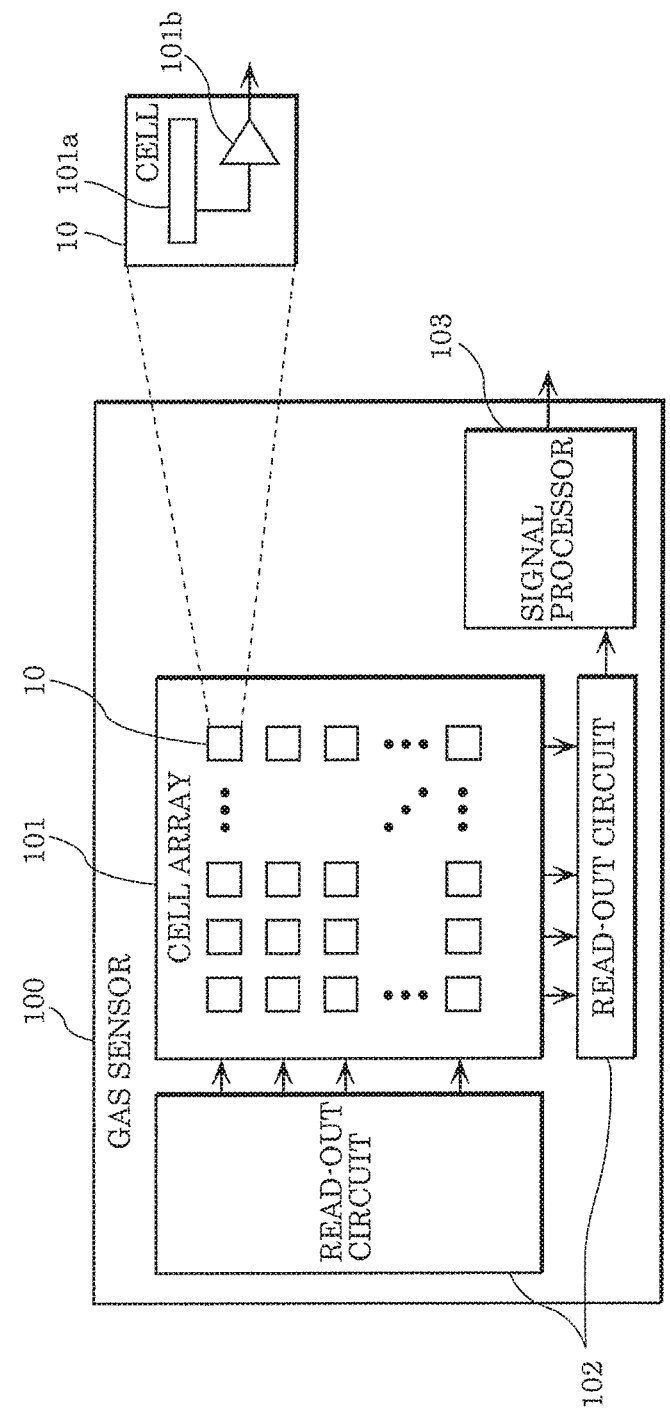
- FIG. 1 is an example of the configuration of a gas sensor according to Embodiment 1.

FIG. 1 is a block diagram illustrating an example of the functional configuration of the gas sensor. Gas sensor 100 includes: cell array 101 in which a plurality of cells 10 each of which includes gas molecule detector 101*a* and amplifier circuit 101*b* are disposed in rows and columns (for example, the size ranges approximately from 10 rows and 10 columns to 1000 rows and 1000 columns); read-out circuit 102 which reads out signals outputted from each of the plurality of cells 10; and signal processor 103 which processes the signals read out. The number of cells 10 is not particularly limited, and the number may be adjusted appropriately as necessary.

In each cell 10, change in the output is amplified by amplifier circuit 101*b*. The change is caused by exchanging electric charge when gas molecules are absorbed to gas molecule detector 101*a*. The amplified signals are read out by read-out circuit 102 disposed for rows and columns of the cells, and the signals read out are outputted by signal processor 103 as intended data. For example, when signal processor 103 is an image processor, the read-out signal can be imaged.

Figure 2:
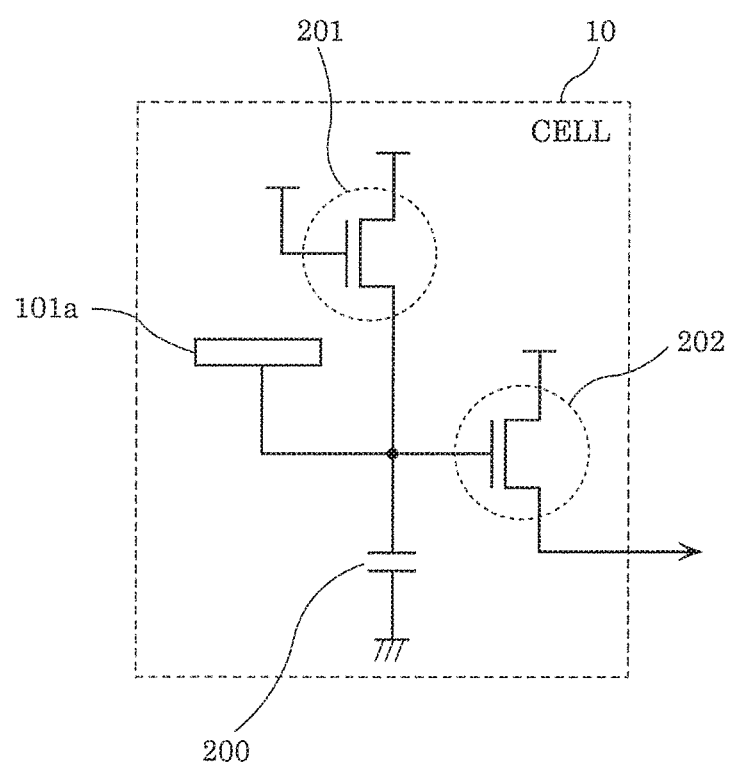
FIG. 2 is a circuit diagram of an example of the cell configuration of the gas sensor according to Embodiment 1.

FIG. 2 is a block diagram illustrating an example of the configuration of cell 10. Each cell 10 includes: gas molecule detector 101*a*; charge accumulation area 200 which is electrically connected to gas molecule detector 101*a*; and reset transistor 201 which resets charge accumulation area 200. The potential of gas molecule detector 101*a* is set to a power supply potential of reset transistor 201.

In the example of FIG. 2, amplification transistor 202 is used as an example of amplifier circuit 101*b*. The electric charge exchanged when gas molecules are absorbed to gas molecule detector 101*a* is accumulated in charge accumulation area 200. Amplification transistor 202 amplifies the change in voltage due to the change in the amount of electric charge accumulated in charge accumulation area 200, and outputs it as a signal. The outputted signal is transmitted to signal processor 103 through a column signal line (not illustrated). A single column signal line may be provided for each column of cells or for each cell 10, or may be provided per certain number of cells 10 in the same column.

The electric charge accumulated in charge accumulation area 200 is reset by reset transistor 201. Gas molecule detector 101a is electrically isolated between adjacent ones of cells 10. When an output signal from each cell 10 is to be read out, each cell 10 may further include a selection transistor. Read-out circuit 102 specifies cell 10 from which a signal is to be outputted.

After the gas molecule detection, reset transistor 201 is turned on, and the potential of gas molecule detector 101a is changed. As a result, since gas molecules can be desorbed by the Coulomb repulsion between the gas molecules and gas molecule detector 101a, a reset operation is possible even if there is no temperature controller such as that in Japanese Unexamined Patent Application Publication No. 2012-112651.

As described above, detecting gas molecules by gas sensor 100 according to the present embodiment is not performed by detecting change in the resistance value such as that in Japanese Unexamined Patent Application Publication No. 2012-112651, but performed by reading out electric charge. Therefore, since it is unnecessary to control to the temperature according to gas molecules in gas sensor 100, a temperature controller such as that in Japanese Unexamined Patent Application Publication No. 2012-112651 is not required, and miniaturization and cost reduction of gas sensor 100 can be achieved. Moreover, since the reset operation is performed by controlling the voltage pulse applied to reset transistor 201, time can be shortened compared with when the resetting is performed with the conventional temperature control.

Moreover, since the output can be increased by reducing the capacity of charge accumulation area 200, it is not necessary to enlarge the sensing part as in Japanese Unexamined Patent Application Publication No. 59-142452, or add a structure such as that in Japanese Unexamined Patent Application Publication No. 2004-085392. Thus, miniaturization is possible.

Note that, it is needless to say that detection and desorption of gas molecules is possible not only with a plurality of cells 10. The detection and desorption can be performed in a similar way also with a single cell 10.

Figure 3:
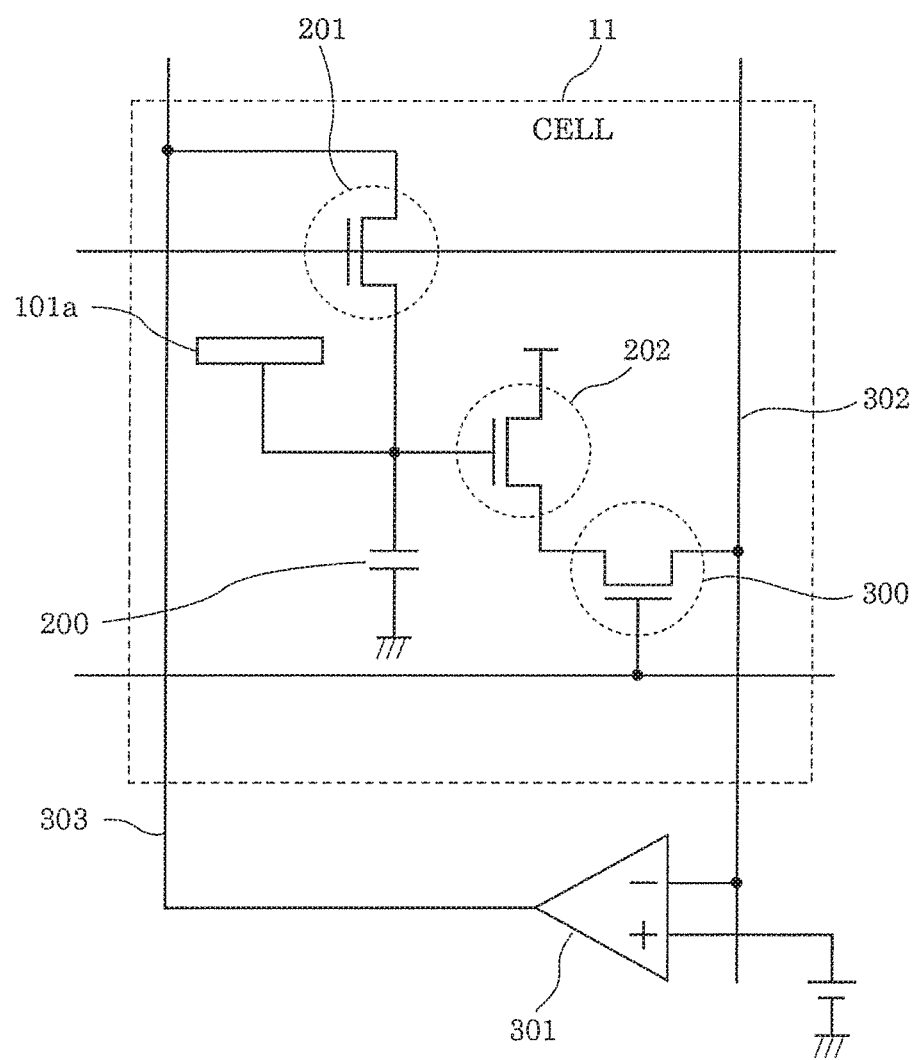
FIG. 3 is a circuit diagram illustrating an example of the cell configuration of a gas sensor according to a variation of Embodiment 1.

FIG. 3 is a circuit diagram illustrating an example of the configuration of cell 11 according to a variation. Cell 11 includes: gas molecule detector 101a, charge accumulation area 200, reset transistor 201, amplification transistor 202, selection transistor 300, feedback amplifier circuit 301, column signal line 302, and feedback line 303.

The source terminal of selection transistor 300 is connected to the source terminal of amplification transistor 202, and the drain terminal of selection transistor 300 is connected to column signal line 302. The source terminal of reset transistor 201 is connected to charge accumulation area 200, and the drain terminal of reset transistor 201 is connected to feedback line 303.

Regarding feedback amplifier circuit 301 disposed for each column, since an inverting input is connected to column signal line 302, a non-inverting input is connected to a fixed voltage, and an output is connected to feedback line 303, a feedback signal obtained by inverting and amplifying the signal from a cell is outputted. With this configuration, when the signal charge accumulated, in charge accumulation area 200 is reset by reset transistor 201, a feedback signal according to an output signal is supplied to the drain terminal of reset transistor 201 via feedback amplifier circuit 301. Consequently, kTC noise resulting from thermal noise of reset transistor 201 is suppressed, and highly sensitive detection is possible.

Figure 4:
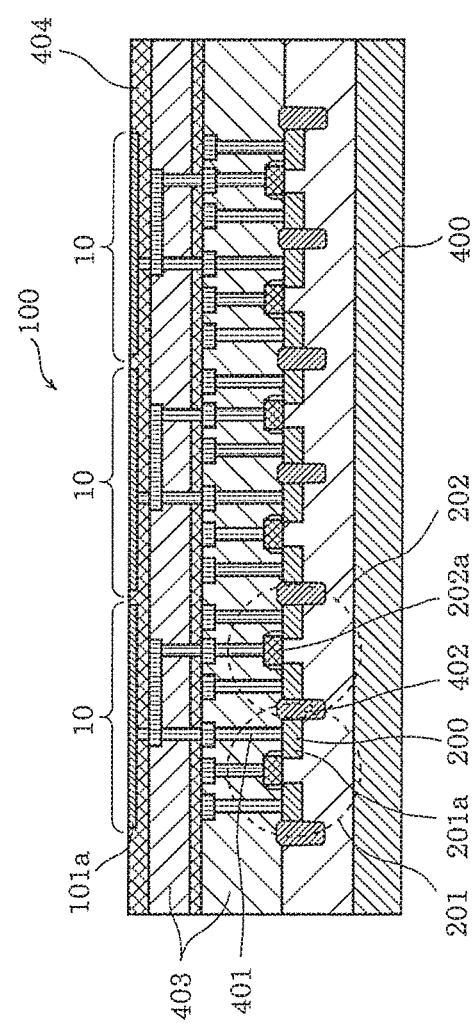
FIG. 4 is a cross-sectional view illustrating an example of the structure of a region including three cells of the gas sensor according to Embodiment 1.

FIG. 4 is a cross-sectional view illustrating an example of the structure of regions of three cells of gas sensor 100. The cross-sectional structure of each cell 10 is described with reference to FIG. 4. A similar cross-sectional structure may be applied to cell 11. Above semiconductor substrate 400, charge accumulation area 200, reset transistor 201 which resets charge accumulation area 200, and amplification transistor 202 which amplifies electric charge accumulated in charge accumulation area 200 are included. Charge accumulation area 200 also functions as source 201a of reset transistor 201. Charge accumulation area 200 is electrically connected to gate terminal 202a of amplification transistor 202 and gas molecule detector 101a, via contact plug 401. Although not illustrated, cell 11 may include selection transistor 300 in the same cell.

Each transistor is electrically isolated by element isolation region 402 which is a shallow trench isolation (STI) region which is formed from $SiO_2$, for example. Moreover, interlayer insulating film 403 is disposed between gas molecule detector 101a and each transistor. Contact plug 401 is formed from metal such as copper (Cu) and tungsten (W), or a semiconductor such as polysilicon. When contact plug 401 includes polysilicon, contact plug 401 may have a conductivity type same as the conductivity type of charge accumulation area 200. In this case, impurities are diffused from contact plug 401 to charge accumulation area 200, and it is possible to form an ohmic contact. Moreover, a leak can be suppressed when the impurity concentration of charge accumulation area 200 is lowered.

When contact plug 401 is formed from a material having a high resistance, it also enables contact plug 401 to function as a temperature controller at the time of detecting gas. The relationship between the amount of heat generation (Q) and the resistance value (R) per unit time is expressed as $Q = R \times I \times I$ (I: the amount of current).

Gas molecule detector 101a is disposed on insulating film 404 (silicon nitride (SiN), for example) which is flattened. The upper surface of gas molecule detector 101a and the upper surface of insulating film 404 may be flush with each other, or the upper surface of gas molecule detector 101a may be at a position higher than the upper surface of insulating film 404. Here, "flush with each other" means being substantially flush with each other including some manufacturing tolerances. Gas molecule detector 101a is electrically isolated from a gas molecule detector of an adjacent cell.

Gas molecule detector 101a includes a material which exchanges electric charge by the oxidation-reduction reaction that occurs when gas molecules are adsorbed. Gas molecule detector 101a includes, for example, an oxide or a nitride such as $SnO_2$, $WO_3$, $ZnO$, $ZrO_2$, and TiN. With this configuration, when gas molecules are adsorbed to gas molecule detector 101a, electric charge is exchanged by the oxidation-reduction reaction between gas molecules and gas molecule detector 101a. Change in the voltage due to the change in the amount of electric charge accumulated in charge accumulation area 200 is detectable as a signal output.

Depressions and projections may be formed on the surface of gas molecule detector 101a by a physical surface treatment in forming a film. With this configuration, the surface area for adsorbing gas molecules can be expanded and the sensitivity can be increased.

When gas molecule detector 101a is TiN, since Ti of the outermost surface is oxidized under an anticipated-use environment, the outermost surface is titanium oxide ($TiO_2$). When gas molecules cannot pass through $TiO_2$ of the outermost surface, the gas molecules will not be detected. Therefore, $TiO_2$ of the outermost surface can be used as a filter which distinguishes the gas molecules which should be detected, hereinafter referred to as target gas molecules.

Insulating film 404 may be an adsorbent which is formed from an oxide such as silica and alumina, for example. As an example, the case is considered where the target gas molecules are negatively ionized, and gas which is unnecessary to be detected, hereinafter referred to as unwanted gas, is positively ionized in the same space. When insulating film 404 is silica, the surface of silica is negatively charged. Thus, this increases the possibility that the target gas molecules are not adsorbed to insulating film 404, but are adsorbed to gas molecule detector 101a which is positively charged. Since the unwanted gas is positively charged, this increases the possibility that the gas molecules are not adsorbed to gas molecule detector 101a, but are adsorbed to insulating film 404.

As a result, the output change by the unwanted gas is suppressed, and the detection sensitivity for the gas which should be detected, hereinafter referred to as target gas, increases. Since the surface of alumina is positively charged, the target gas molecules are positively ionized. When the unwanted gas is negatively ionized, using alumina as insulating film 404 increases the detection sensitivity for the target gas molecules.

As described above, gas molecules to be detected can be specified by selecting the material of insulating film 404 according to the ionization state of the target gas. This is not limited to the configuration in which insulating film 404 itself functions as an adsorbent. A similar effect can be obtained when an adsorbent is separately formed between gas molecule detectors 101a on insulating film 404.

Insulating film 404 may be a catalyst which includes a metallic oxide, etc. For example, $TiO_2$ forms active oxygen with strong oxidation power. The case is considered where the bonding of the target gas molecules is less likely to be oxidized and decomposed by active oxygen, and the bonding of the gas molecules which are unnecessary to be detected, hereinafter referred to as unwanted gas molecules, are easily oxidized and decomposed by active oxygen, and both gases are present in the same environment. Since the unwanted gas molecules are oxidized and decomposed by the active oxygen which is formed by titanium oxide, the unwanted gas molecules are less likely to be adsorbed to gas molecule detector 101a, and the detection sensitivity for the target gas molecules increases.

This is not limited to the configuration in which insulating film 404 itself functions as a catalyst. A similar effect can be obtained even when a catalyst is separately formed between gas molecule detectors 101a on insulating film 404. Furthermore, this is not limited to the configuration in which a catalyst is formed between gas molecule detectors. A similar effect can be obtained even when gas molecule detector 101a of at least one cell is formed from a material (for example, $TiO_2$) having a similar effect as the catalyst.

Embodiment 2

Figure 5A:
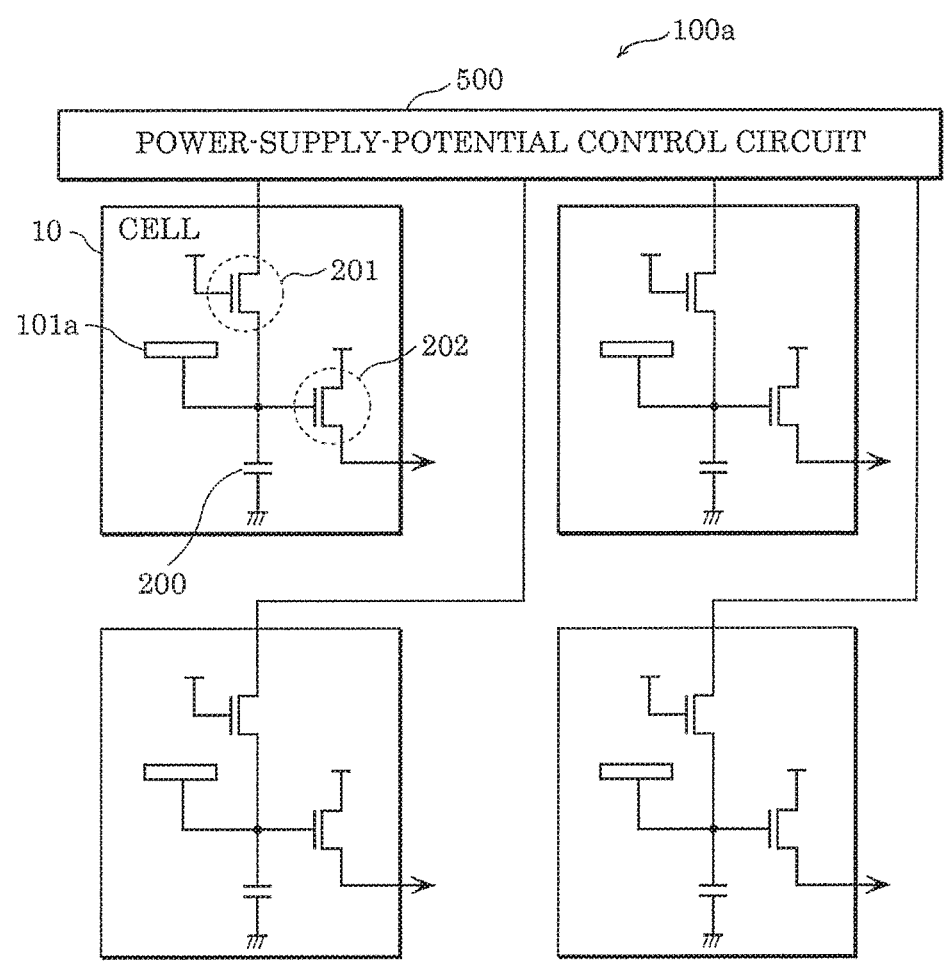
FIG. 5A is a circuit diagram illustrating an example of the cell configuration of a gas sensor according to Embodiment 2.
Figure 5B:
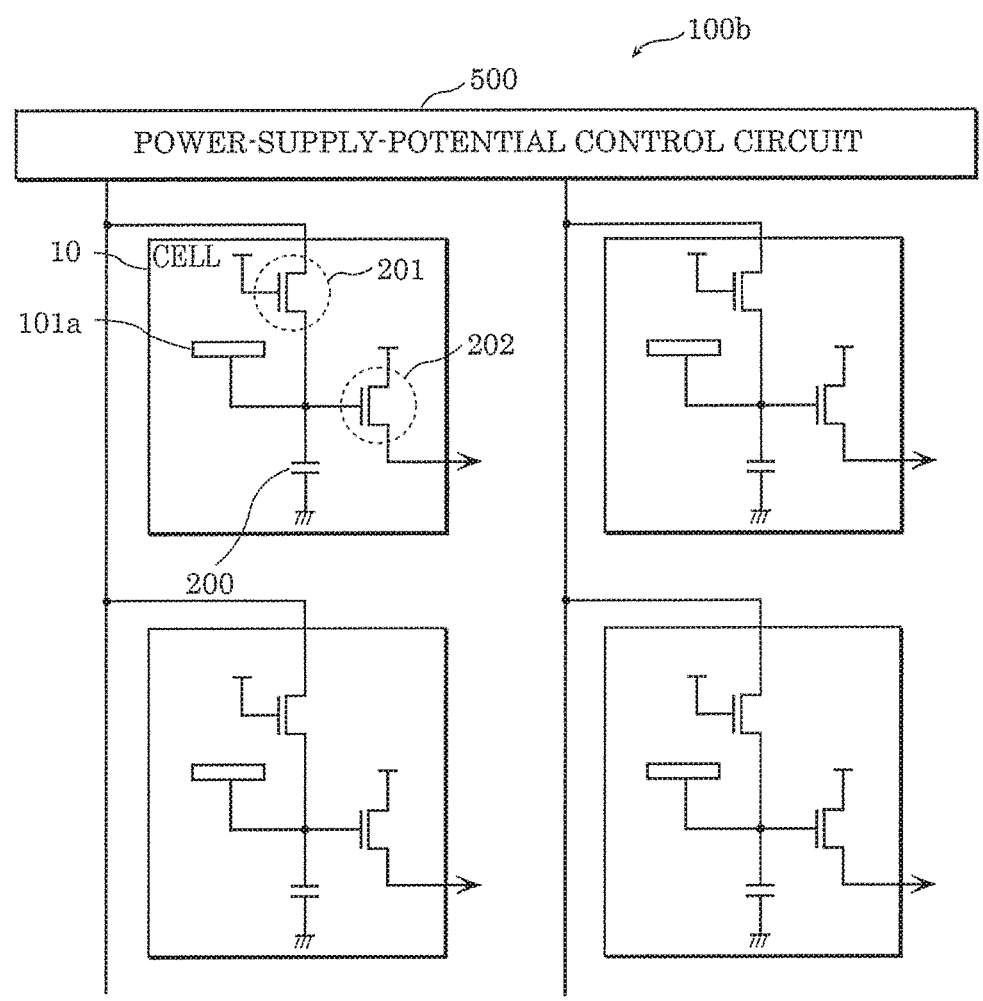
FIG. 5B is a circuit diagram illustrating an example of the cell configuration of the gas sensor according to Embodiment 2.

FIG. 5A and FIG. 5B are block diagrams respectively illustrating exemplary configurations of gas sensors 100a and 100b according to Embodiment 2. Each cell 10 has gas molecule detector 101a, amplification transistor 202, charge accumulation area 200, and reset transistor 201. Each of gas sensors 100a and 100b has power-supply-potential control circuit (first control circuit) 500 connected to reset transistors 201.

As illustrated in FIG. 5A, since power-supply-potential control circuit 500 is connected to the drain terminal of reset transistor 201 of each cell 10, an intended reset potential can be set for each cell 10 by power-supply-potential control circuit 500. As illustrated in FIG. 5B, when a connecting line between the drain terminal of reset transistors 201 and power-supply-potential control circuit 500 is shared by each column, an intended reset potential can be set for each column.

With the above configuration, the potential of gas molecule detector 101a which is electrically connected to charge accumulation area 200 is controllable for each cell 10 or each column of cells 10. When each cell is controlled, the number of lines increases compared with when each column of cells 10 is controlled. However, this provides more flexibility in setting a reset potential for cell array 101.

An example of setting the reset potential by power-supply-potential control circuit 500 is described.

Example 1

For example, the case is considered where the target gas molecules are negatively charged and the unwanted gas molecules are positively charged, and the target gas molecules and the unwanted gas molecules are present in the same environment. In cell array 101, when the potential of gas molecule detector 101a in a first region which includes at least one cell 10 used for detection is positive and the potential of gas molecule detectors 101a in a second region which includes cells other than the at least one cell 10 is negative, the unwanted gas molecules are attracted by the Coulomb force to gas molecule detector 101a in the second region, and the target gas molecules are attracted by the Coulomb force to gas molecule detector 101a in the first region. Therefore, in this case, the detection sensitivity for the target gas molecules can be increased.

When the unwanted gas molecules are included among the gas molecules having the negative polarity, they are dissociated by the following method. The Coulomb force which attracts gas molecules to gas molecule detector 101a is different depending on gas molecules according to the configurations of the molecules. Therefore, when the potential of gas molecule detector 101a is slightly changed to a positive side, and the timing at which the gas molecules are detected is shortened as much as possible, molecules with strong Coulomb force are attracted to gas molecule detector 101a earlier, and contribute to the output change. As compared with this, since molecules with weak Coulomb force take more time before being attracted to gas molecule detector 101a and contributing to the output change, their peaks of the output change differ. A target molecule can be specified by obtaining beforehand the data representing the output change time for the target molecule. As another example of the gas identifying method, a filter for selecting a gas molecule may be included in the package of a gas sensor.

Example 2

In the case where gas molecules (for example, p-aminophenol) which repeat the oxidation-reduction reaction are to be detected, when the gas molecules which are positively charged are adsorbed to gas molecule detector 101a, gas molecules are oxidized and turn into other gas molecules (p-quinone imine). The other gas molecules (p-quinone imine) are reduced when they are adsorbed to gas molecule detector 101a that is negatively charged, and the other gas molecules change into the original gas molecules (p-aminophenol).

With this configuration, since the oxidation-reduction reaction of gas molecules do not end with a one-time reaction during adsorption to gas molecule detector 101a, but occurs continuously, the changed amount of electric charge per gas molecule increases, and the sensitivity can be increased.

In this case, the polarities of the power supply potentials of the reset transistors, i.e., the polarities of the potentials may be mutually differ between gas molecule detectors 101a of adjacent ones of the columns or adjacent ones of the cells, for example. When the oxidation-reduction reaction can be repeated between neighboring cells, the electric charge of an amount necessary for detection can be accumulated in a short time.

Embodiment 3

Figure 6A:
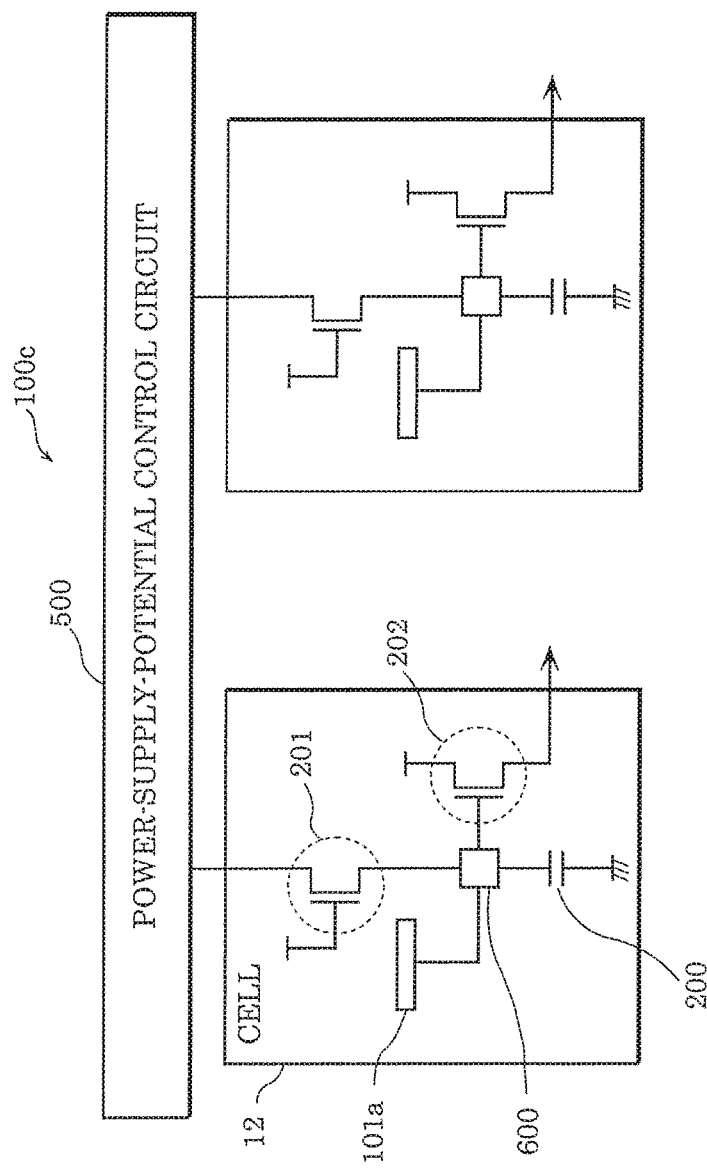
FIG. 6A is a circuit diagram illustrating an example of the cell configuration of a gas sensor according to Embodiment 3.

FIG. 6A is a block diagram illustrating an example of the configuration of cell 12 of gas sensor 100c according to Embodiment 3. Each cell 12 includes charge transfer controller 600 for suppressing movements of the electric charge of gas molecule detector 101a during the operation of reset transistor 201.

Figure 6B:
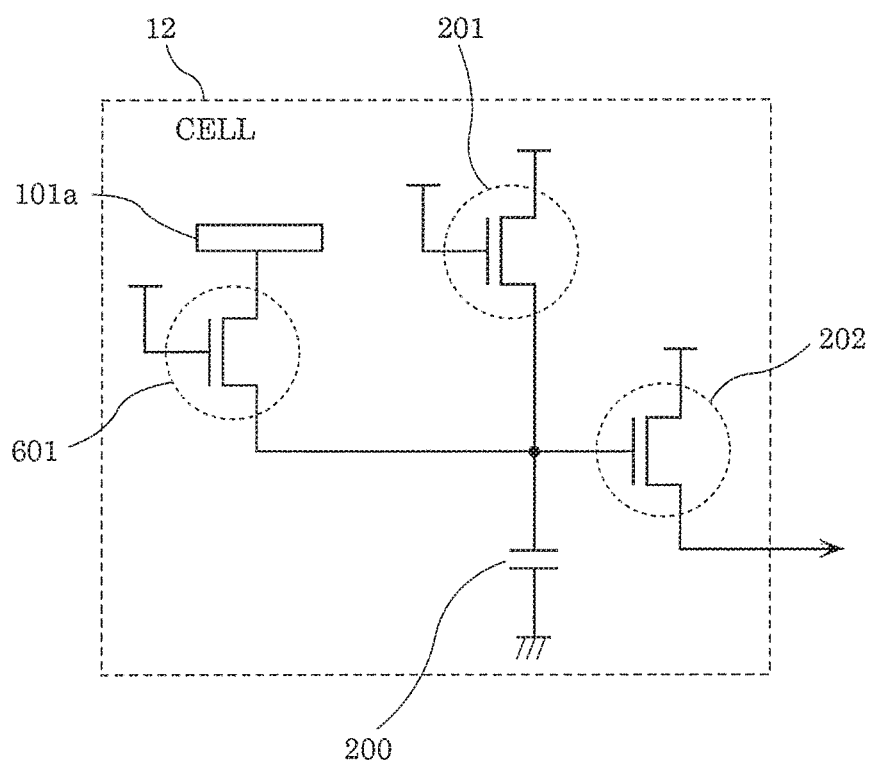
FIG. 6B is a circuit diagram illustrating an example of the cell configuration of the gas sensor according to Embodiment 3.
Figure 6C:
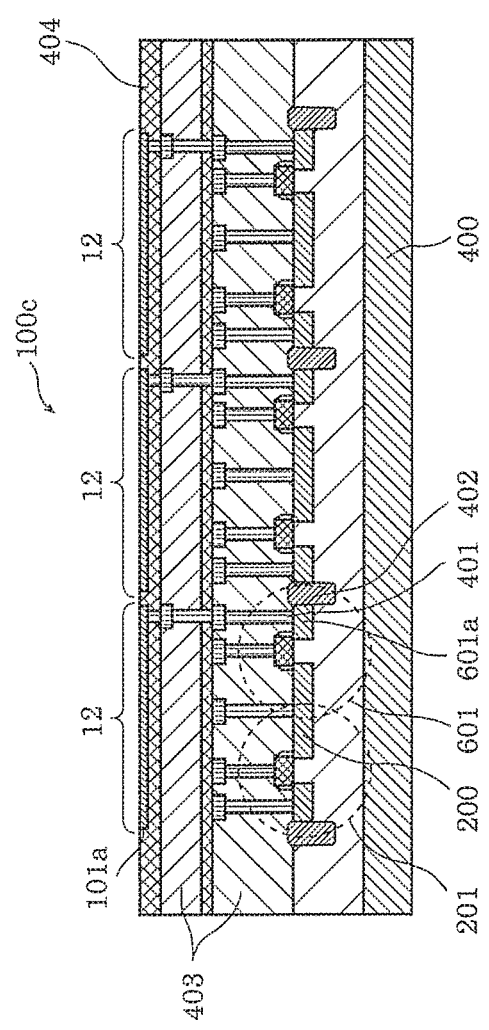
FIG. 6C is a cross-sectional view illustrating an example of the structure of regions of three cells of the gas sensor according to Embodiment 3.

Regarding a specific example of gas sensor 100c, the circuit configuration of cell 12 is illustrated in FIG. 6B, and the cross-sectional structure of a region including three cells is illustrated in FIG. 6C. Each cell 12 includes transfer transistor 601 as an example of charge transfer controller 600 between gas molecule detector 101a and charge accumulation area 200. Gas molecule detector 101a is connected to diffusion region 601a of transfer transistor 601 by contact plug 401 which is conductive. When reset transistor 201 is an ON state, transfer transistor 601 is controlled to be an OFF state. Transfer transistor 601 is not limited to charge transfer controller 600. Other elements may be used as long as the movements of the electric charge in gas molecule detector 101a can be suppressed during the operation of reset transistor 200.

With this configuration, change in the electric charge in gas molecule detector 101a can be detected not only after the reset operation is finished, but also from when the reset operation is started to when the reset operation is finished. Therefore, this configuration is effective particularly when a gas molecule to be detected is in low concentration. Noise is also removable when correlated double sampling is used.

Embodiment 4

Figure 7:
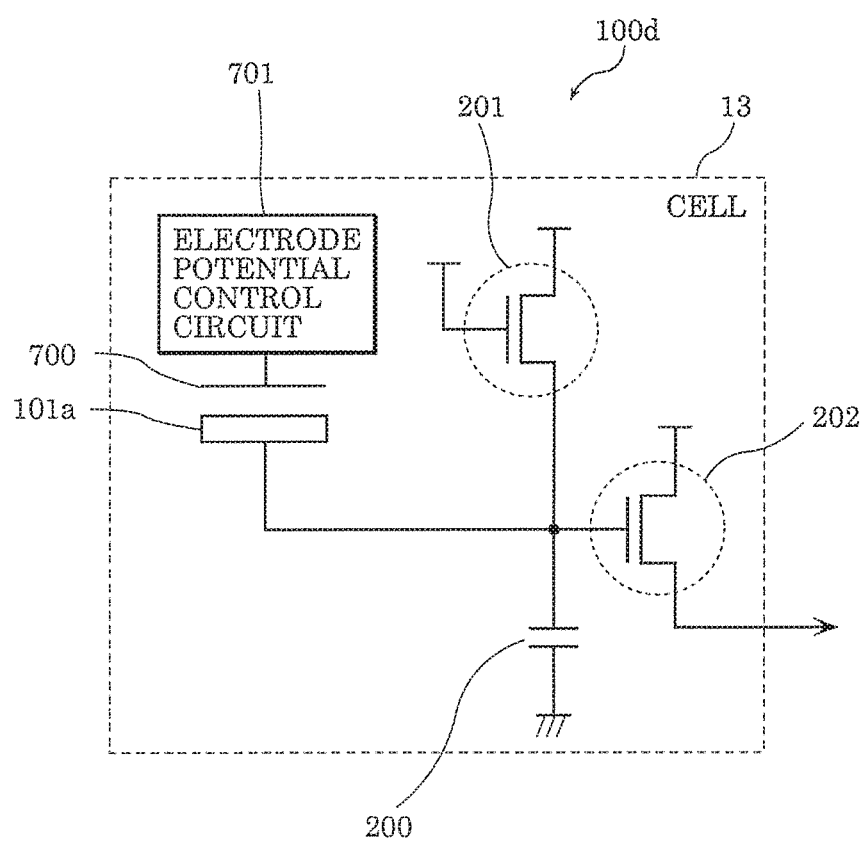
FIG. 7 is a circuit diagram illustrating an example of the cell configuration of a gas sensor according to Embodiment 4.

FIG. 7 is a circuit diagram illustrating an example of the configuration of gas sensor 100d of cell 13 according to Embodiment 4.

Cell 13 includes charge accumulation area 200 which is electrically connected to gas molecule detector 101a; reset transistor 201 which resets charge accumulation area 200; amplification transistor 202 which amplifies an output; upper electrode 700 which is disposed above gas molecule detector 101a and faces gas molecule detector 101a; and electrode potential control circuit (second control circuit) 701 which controls the potential of upper electrode (first electrode) 700.

Figure 8A:
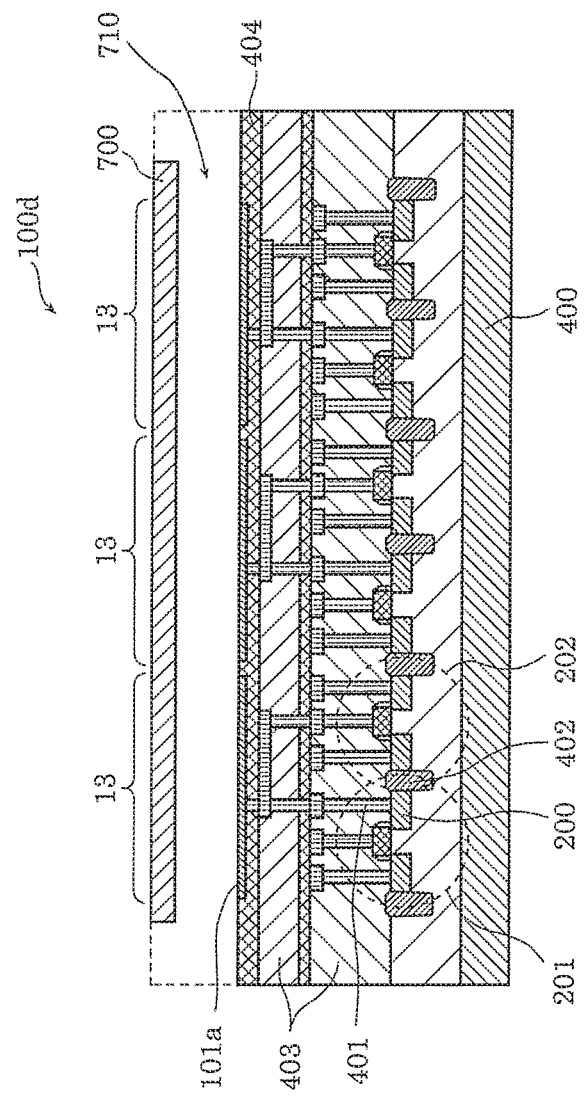
FIG. 8A is a cross-sectional view illustrating an example of the structure of a region including three cells of the gas sensor according to Embodiment 4.

FIG. 8A is a cross-sectional view illustrating an example of the structure of a region including three cells of gas sensor 100d. Gas sensor 100d is configured by adding electrode 700 to gas sensor 100 illustrated in FIG. 4. Electrode 700 is supported by a support provided to another cross-section which is not illustrated in FIG. 8A. The region (hollow section 710) between gas molecule detectors 101a and upper electrode 700 is hollow and communicates with the environment where the target gas molecules are present.

It is assumed that the target gas molecules are negatively charged, the unwanted gas molecules are positively charged, and each group of gas molecules are present in the same environment. When the power supply potential of reset transistor 201 of cell 13 which is disposed in a peripheral part of cell array 101 and the potential of upper electrode 700 have positive polarity, the target gas molecules are negatively charged, and thus the gas molecules are led to hollow section 710. As compared with this, the unwanted gas molecules having positive polarity are blocked from entering into hollow section 710 by the Coulomb repulsive force.

Figure 8B:
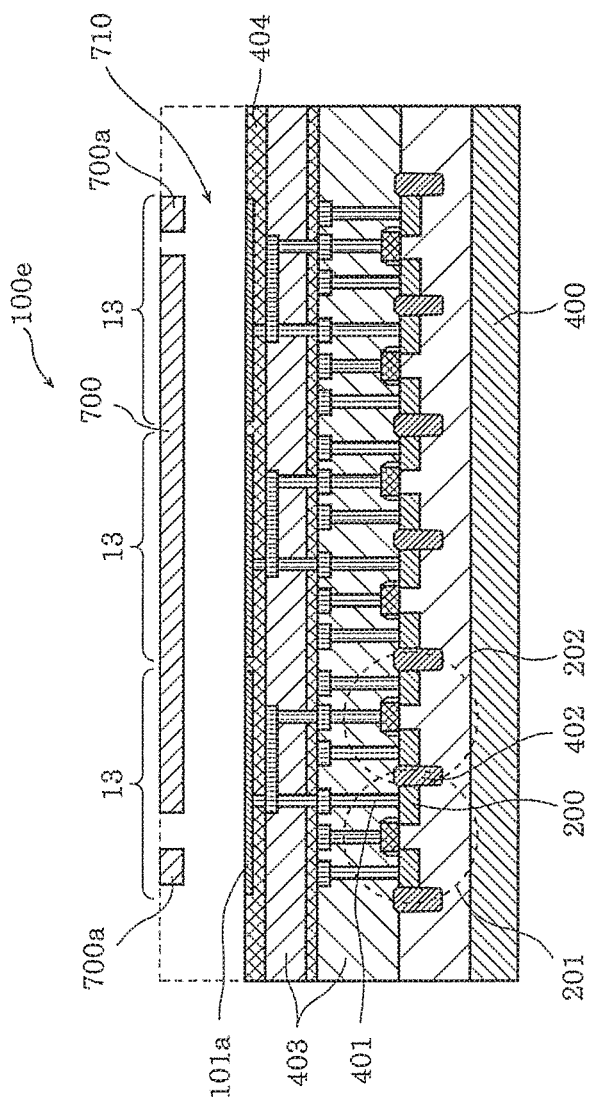
FIG. 8B is a cross-sectional view illustrating an example of the structure of a region including three cells of the gas sensor according to a variation of Embodiment 4.
Figure 8C:
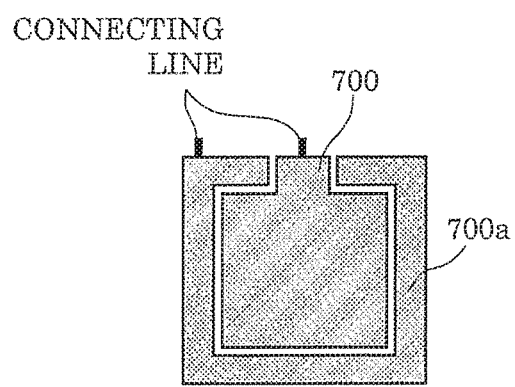
FIG. 8C is a plan view illustrating an example of a gas molecule detector of the gas sensor according to the variation of Embodiment 4.

FIG. 8B and FIG. 8C are respectively a cross-sectional view and a plan view of gas sensor 100e according to a variation of the present embodiment. In a plan view, gas sensor 100e further includes peripheral electrode (second electrode) 700a which surrounds upper electrode 700, and which is electrically isolated (insulated) from upper electrode 700. Each of upper electrode 700 and peripheral electrode 700a has a connecting line for connecting to electrode potential control circuit 701.

With this configuration, the number of molecules which are adsorbed to gas molecule detector 101a can be increased, and the sensitivity can be increased by, for example, changing the potential of upper electrode 700 from positive to negative, and desorbing the gas molecules currently adsorbed by the Coulomb repulsive force, after the negatively-charged target gas molecules are adsorbed to the positively charged upper electrode 700. During that time, when the positive polarity of peripheral electrode 700a is maintained, the negatively-charged target gas molecules can be continuously introduced into hollow section 710 without interruption.

A method of forming hollow section 710 in gas sensors 100d and 100e is described.

FIG. 9A to FIG. 9H are process flow diagrams illustrating an example of the method of forming hollow section 710 in gas sensors 100d and 100e. Hollow section 710 is formed as follows in accordance with the process illustrated from FIG. 9A to FIG. 9H, for example.

Figure 9A:
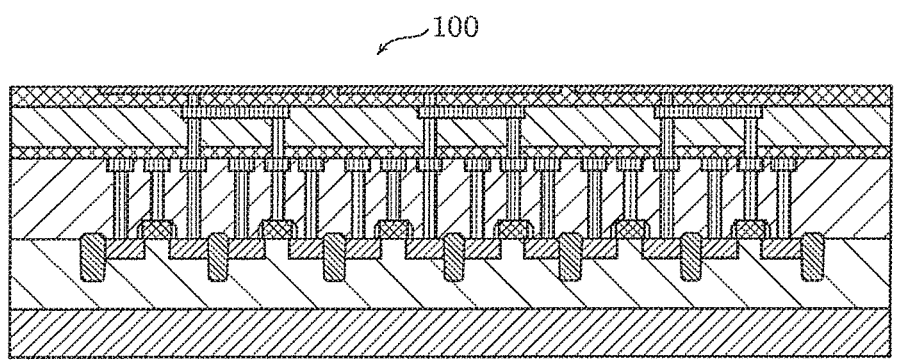
FIG. 9A is a cross-sectional view illustrating an example of a method of forming a hollow section of the gas sensor according to Embodiment 4.

Gas sensor 100 according to Embodiment 1 is formed (FIG. 9A). The method of forming gas sensor 100 is not particularly limited. Gas sensor 100 may be formed using a common manufacturing method of an image sensor, for example.

Figure 9B:
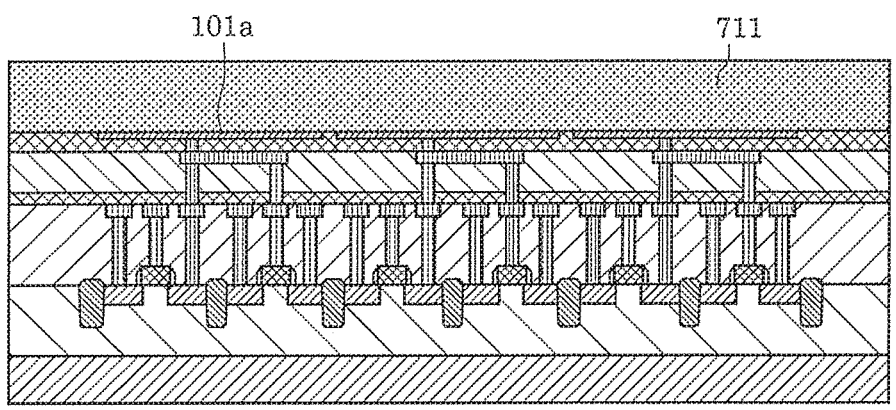
FIG. 9B is a cross-sectional view illustrating an example of the method of forming the hollow section of the gas sensor according to Embodiment 4.

On gas molecule detectors 101a, sacrifice layer 711 (for example, amorphous silicon) is formed (FIG. 9B). Sacrifice layer 711 is removed later by etching. The region where sacrifice layer 711 is removed is hollow section 710. In order to form support supporting upper electrode 700, a part of sacrifice layer 711 in another cross-section which is not illustrated in FIG. 9B (for example, a corner part of a cell) is removed.

Figure 9C:
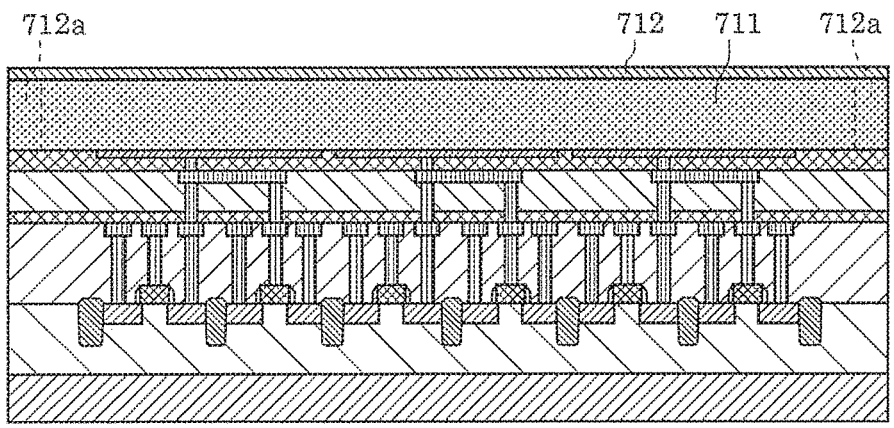
FIG. 9C is a cross-sectional view illustrating an example of the method of forming the hollow section of the gas sensor according to Embodiment 4.

Protective film 712 (for example, silicon oxide) is formed (including flattening) on sacrifice layer 711 and in the portion in which sacrifice layer 711 is removed (FIG. 9C). At this time, the protective film embedded into the portion in which sacrifice layer 711 is removed in another cross-section serves as support 712a later.

Figure 9D:
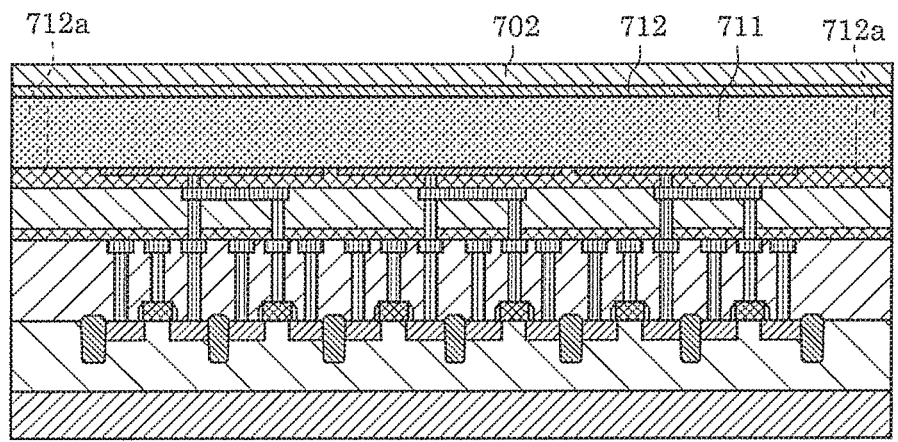
FIG. 9D is a cross-sectional view illustrating an example of the method of forming the hollow section of the gas sensor according to Embodiment 4.

A film of Al etc. is formed as electrode material 702 on protective film 712 (FIG. 9D).

Figure 9E:
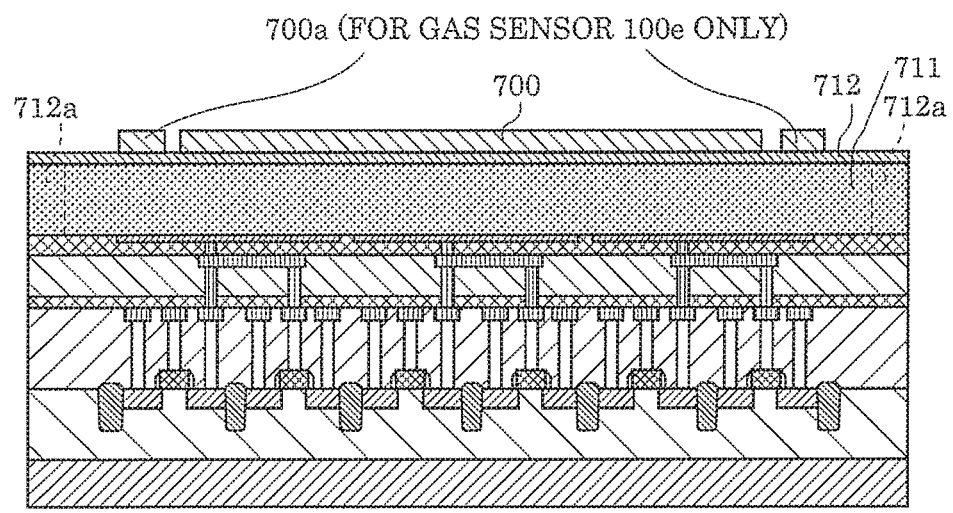
FIG. 9E is a cross-sectional view illustrating an example of the method of forming the hollow section of the gas sensor according to Embodiment 4.

Upper electrode 700 is formed by patterning electrode material 702. In gas sensor 100e, peripheral electrode 700a surrounding upper electrode 700 is also formed (FIG. 9E).

Figure 9F:
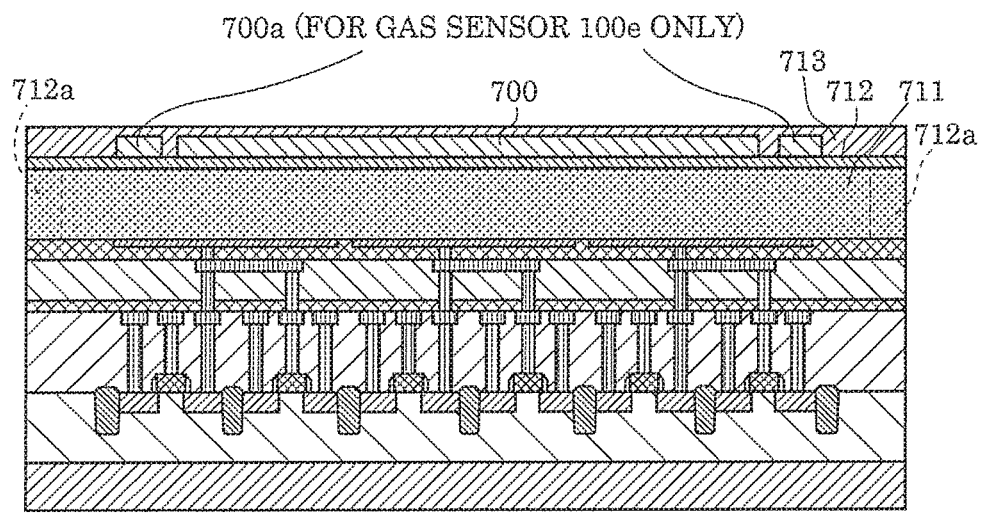
FIG. 9F is a cross-sectional view illustrating an example of the method of forming the hollow section of the gas sensor according to Embodiment 4.

On upper electrode 700 (and peripheral electrode 700a), protective film 713 (for example, nitride film) is formed (FIG. 9F).

Figure 9G:
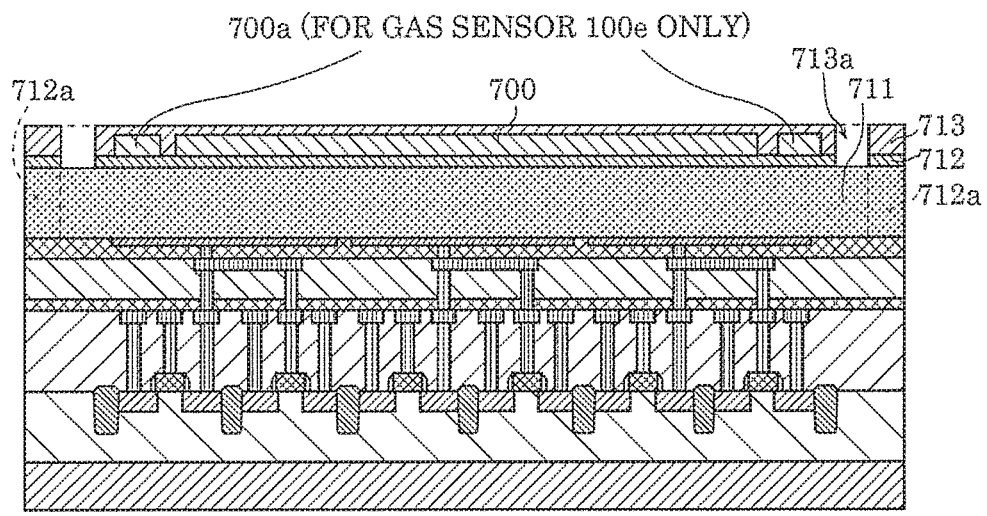
FIG. 9G is a cross-sectional view illustrating an example of the method of forming the hollow section of the gas sensor according to Embodiment 4.

Introducing holes 713a which penetrate through protective film 713 and protective film 712 are formed by lithography (FIG. 9G).

Figure 9H:
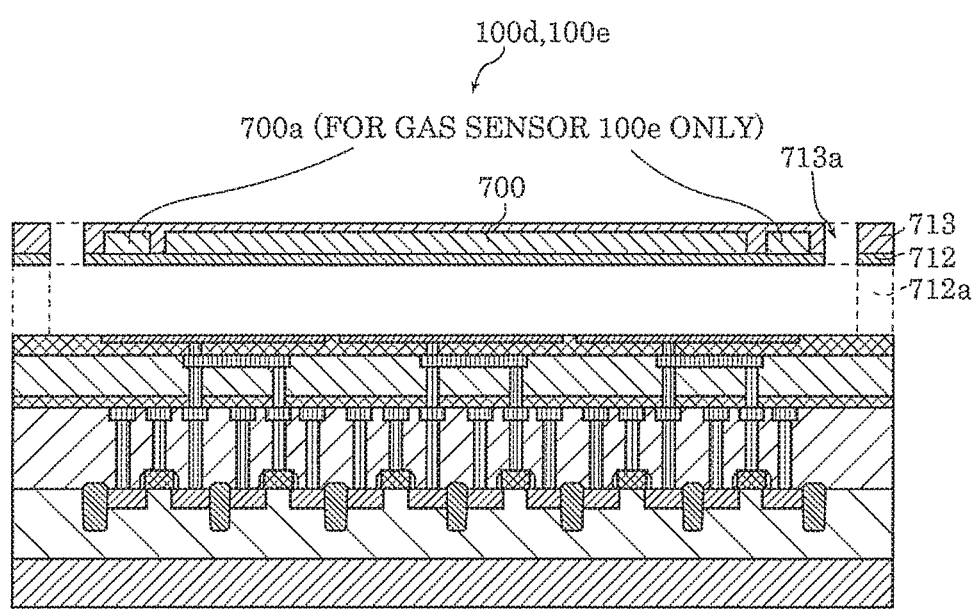
FIG. 9H is a cross-sectional view illustrating an example of the method of forming the hollow section of the gas sensor according to Embodiment 4.

Gas etchant (for example, $ClF_3$) which has a selection ratio between the material of sacrifice layer 711 and the material of protective film 712 is introduced via introducing holes 713a to remove sacrifice layer 711 and form hollow section 710 (FIG. 9H). At this time, the undersurface of upper electrode 700 (and peripheral electrode 700a) is protected from gas etching by protective film 712. Upper electrode 700 (and peripheral electrode 700a) is supported by support 712a. Hollow section 710 communicates with the environment where the target gas molecules are present via introducing holes 713a and openings formed on side surfaces of gas sensor 100e.

Gas sensors 100d and 100e each having hollow section 710 and upper electrode 700 (and peripheral electrode 700a) are formed through the above process.

In gas sensors 100d and 100e each having hollow section 710, motions of gas molecules in hollow section 710 can be controlled by changing with time the polarity of the power supply potential of a reset transistor for each of the cells. Controlling the motions of gas molecules in gas sensors 100d and 100e will be described.

Figure 10A:
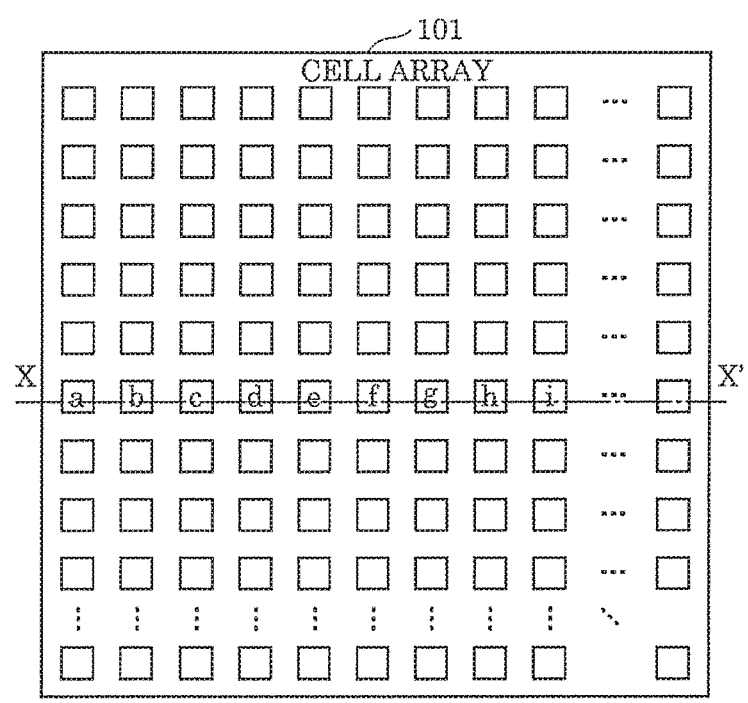
FIG. 10A is a plan view illustrating an example of the arrangement of a plurality of cells in a cell array.

FIG. 10A is a plan view illustrating arrangement of nine cells (a, b, c, d, e, f, g, h, and i) along the X-X' line of cell array 101. Cell a is positioned on the peripheral side of cell array 101, and cell i is positioned on the central side of cell array 101, in the direction of X-X'.

FIG. 10B shows an example of the timing chart which indicates change in the polarities of the power supply potentials of reset transistors 201 of the nine cells (a, b, c, d, e, f, g, h, and i) from time t0 to t14, i.e., change in the polarities of the potentials of gas molecule detectors 101a of cells a to i. According to the timing chart, after t7, the polarity of the power supply potential of reset transistor 201 of cell a on the peripheral side is negative, and is in a block state to the positively-charged unwanted gas molecules.

After the target gas molecules are led to hollow section 710, by matching the polarity of the power supply potential of reset transistor 201 of cell a on the peripheral side to the polarity of the target gas molecules, it is possible to allow the gas molecules to stay in hollow section 710 continuously.

After that, the polarities of the power supply potentials of reset transistors 201 are changed in order from the peripheral part of cell array 101 toward the central part. With this configuration, the timings at which the Coulomb attraction and the Coulomb repulsion are generated are changed, and the gas molecules introduced from the outermost periphery can be led to the central part of cell array 101. Consequently, since equipment for introducing gas such as a pump is unnecessary, the miniaturization of a gas sensor can be achieved.

Embodiment 5

Figure 11:
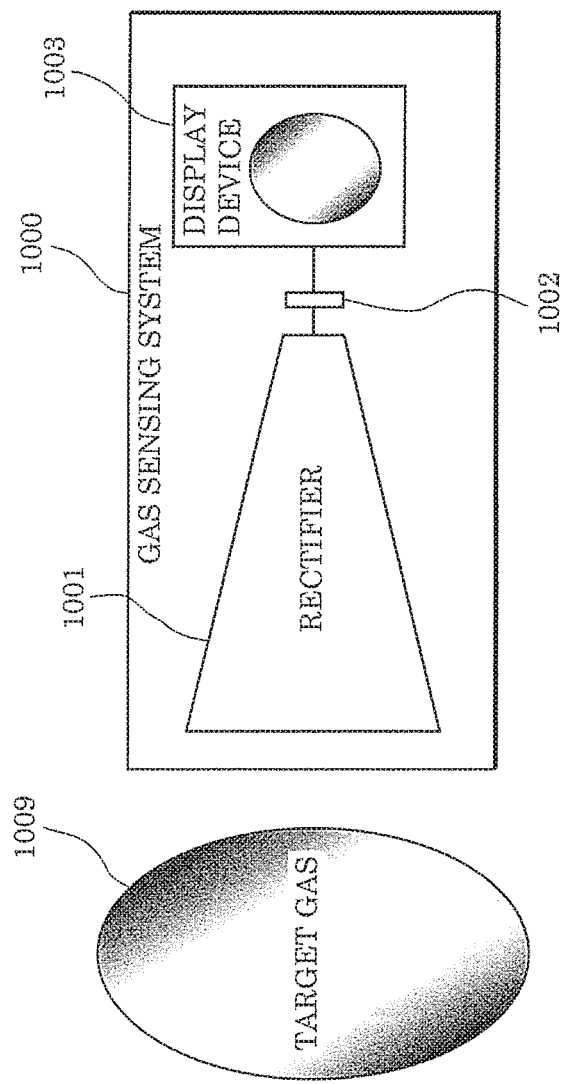
FIG. 11 is a block diagram illustrating an example of the configuration of a gas sensing system according to Embodiment 5.

FIG. 11 is a block diagram illustrating an example of the configuration of a gas sensing system according to Embodiment 5. Gas sensing system 1000 includes: gas sensor 1002; rectifier 1001 which introduces target gas 1009 into cell array 101 of gas sensor 1002 by a laminar flow; and display device 1003 which displays an output of gas sensor 1002. Any of gas sensors 100, and 100a to 100e in the above embodiments may be used as gas sensor 1002.

Since rectifier 1001 is capable of creating a laminar flow, rectifier 1001 is capable of introducing distant target gas 1009 into gas sensor 1002 without changing the distribution of the gas molecules. As a result, gas sensing system 1000 can detect the spatial distribution of gas molecules. A laminar flow can be produced with Reynolds number Re of less than or equal to 2000. Reynolds number Re is expressed as $Re=\rho vL/\mu$ using the density of a fluid $\rho$ (kg/m$^3$), the velocity of a fluid v (m/s), the diameter L (m), and a coefficient of viscosity of a fluid $\mu$ (kg/ms).

Although the gas sensor and the gas sensing system including the same according to the embodiments of the present disclosure have been described above, the present disclosure is not limited to the above embodiments.

Furthermore, each of the processors included in the gas sensor according to the foregoing embodiments is typically implemented as a large-scale integration (LSI) circuit which is an integrated circuit. These processors may be individually configured as single chips or may be configured so that a part or all of the processors are included in a single chip.

Moreover, the method of circuit integration is not limited to LSIs, and implementation through a dedicated circuit or a general-purpose processor is also possible. A field-programmable gate array (FPGA) which allows programming after LSI manufacturing or a reconfigurable processor which allows reconfiguration of the connections and settings of the circuit cells inside the LSI may also be used.

In the above cross-sectional views, although the corners and the sides of each structural component are described linearly, structural components with rounded corners and sides due to manufacturing issues are also included in the present disclosure.

At least a part of the functions may be combined among the functions of gas sensors 100 and 100a to 100e according to the above embodiments, and variations thereof.

Moreover, the numerals used above are all provided as examples for specifically describing the present disclosure, and the present disclosure is not limited to these numerals. The logic levels expressed by high/low or the switching states expressed by ON/OFF are mere examples for specifically describing the present disclosure. An equivalent can be obtained with different combinations of exemplified logic levels or switching states. Furthermore, the above-noted materials of the individual structural components are all provided as examples for specifically describing the present disclosure, and the present disclosure is not limited to these materials. Moreover, the connection relationship between the structural components is provided as an example for specifically describing the present disclosure, and the connection relationship for implementing the functions of the present disclosure is not limited to this.

Although metal-oxide-semiconductor (MOS) transistors are used in the examples in above description, other transistors may be used.

Furthermore, the present disclosure also includes many variations of the embodiment and variations described above within the range conceivable by a person skilled in the art without departing from the purport of the present disclosure.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The present disclosure is applicable to a gas sensor and a gas sensing system including the gas sensor.

What is claimed is:

1. A gas sensor, comprising:
a cell array which includes a plurality of cells disposed in rows and columns;
a read-out circuit which reads out signals from the plurality of cells;
a signal processor which processes the signals read out; and
a first control circuit,
wherein each of the plurality of cells includes:
a gas molecule detector which is electrically isolated between adjacent ones of the plurality of cells; and
an amplifier circuit which is electrically connected to the gas molecule detector,
the cell array includes a first region including at least one cell of the plurality of cells and a second region including cells other than the at least one cell, and
the first control circuit applies potentials having mutually different polarities between (i) the gas molecule detector of the at least one cell in the first region and (ii) the gas molecule detectors of the cells in the second region.

2. The gas sensor according to claim 1,
wherein each of the plurality of cells includes:
a charge accumulation area which is electrically connected to the gas molecule detector; and
a reset transistor which resets the charge accumulation area, and
the amplifier circuit is an amplification transistor which amplifies electric charge accumulated in the charge accumulation area.

3. The gas sensor according to claim 2,
wherein the gas molecule detector is disposed above the charge accumulation area, and is connected to the charge accumulation area by a contact plug which is conductive.

4. The gas sensor according to claim 2, further comprising:
a switch which electrically connects or isolates the gas molecule detector and the charge accumulation area.

5. The gas sensor according to claim 4,
wherein the switch is a transfer transistor, and
the gas molecule detector is disposed above the charge accumulation area, and is connected to a diffusion region of the transfer transistor by a contact plug which is conductive.

6. The gas sensor according to claim 2,
wherein the first control circuit controls a power supply potential of the reset transistors in each of the columns in the cell array.

7. The gas sensor according to claim 6,
wherein the first control circuit applies potentials having mutually different polarities between the gas molecule detectors of adjacent ones of the columns in the cell array.

8. The gas sensor according to claim 2,
wherein the first control circuit controls a power supply potential of the reset transistor in each of the plurality of cells in the cell array.

9. The gas sensor according to claim 8,
wherein the first control circuit applies potentials having mutually different polarities between the gas molecule detectors of adjacent ones of the plurality of cells in the cell array.

10. The gas sensor according to claim 2, further comprising:
a feedback amplifier circuit which supplies a feedback signal according to an output signal of the amplification transistor to a drain terminal of the reset transistor.

11. The gas sensor according to claim 2, wherein the control circuit sequentially changes, while applying a constant potential to the gas molecule detector of one or more cells located at an outer periphery of the cell array, a polarity of a potential applied to the gas molecule detector of cells located inside the one or more cells at the outer periphery of the cell array.

12. The gas sensor according to claim 1, further comprising:
a first electrode which is disposed above the gas molecule detector; and
a second control circuit which controls a potential of the first electrode,
wherein a region between the gas molecule detector and the first electrode is hollow.

13. The gas sensor according to claim 12, further comprising:
a second electrode which is disposed above the gas molecule detector, surrounds the first electrode in a plan view, and is electrically isolated from the first electrode.

14. The gas sensor according to claim 13,
wherein a polarity of the potential of the first electrode differs from a polarity of a potential of the second electrode.

15. The gas sensor according to claim 1, further comprising:
an adsorbent which is disposed between adjacent ones of the gas molecule detectors,
wherein a polarity of electric charge charged on a surface of the adsorbent differs from a polarity of the gas molecule detector.

16. The gas sensor according to claim 1, further comprising:
a catalyst which is disposed between adjacent ones of the gas molecule detectors,
wherein the catalyst decomposes a predetermined gas molecule.

17. A gas sensing system, comprising:
the gas sensor according to claim 1; and
a rectifier which generates a laminar flow,
wherein the rectifier introduces gas molecules into the gas sensor.

* * * * *